United States Patent [19]

Sakamoto et al.

[11] 4,214,589

[45] Jul. 29, 1980

[54] METHOD AND APPARATUS FOR BLOOD PRESSURE MEASUREMENT INCLUDING A TRUE KOROTKOV SOUND DETECTOR

[75] Inventors: Tamaki Sakamoto, Nagaokakyo; Yasunori Ikeda, Kameoka, both of Japan

[73] Assignee: Omron Tateisi Electronics Co., Kyoto, Japan

[21] Appl. No.: 865,449

[22] Filed: Dec. 29, 1977

[30] Foreign Application Priority Data

Sep. 14, 1977 [JP] Japan ................................ 52/111136

[51] Int. Cl.² .............................................. A61B 5/02
[52] U.S. Cl. ..................................... 128/680; 128/715
[58] Field of Search .......... 128/205 A, 205 G, 205 M, 128/205 R, 205 S, 668, 672, 677, 680, 681, 682, 683, 715

[56] References Cited

U.S. PATENT DOCUMENTS

| | | | |
|---|---|---|---|
| 2,827,040 | 3/1958 | Gilford | 128/2.05 A |
| 3,552,383 | 1/1971 | Krueger et al. | 128/2.05 A |
| 3,903,872 | 9/1975 | Link | 128/2.05 A |
| 3,905,354 | 9/1975 | Lichowsky | 128/2.05 M |
| 4,026,277 | 5/1977 | Toda et al. | 128/2.05 A |
| 4,105,020 | 8/1978 | Matsuoka et al. | 128/2.05 A |

OTHER PUBLICATIONS

Schulze et al., Southwestern Institute of Electrical and Electronics Engineering Conference Record, Apr. 1968, pp. 17f1–17f2.

*Primary Examiner*—William E. Kamm
*Attorney, Agent, or Firm*—Stevens, Davis, Miller & Mosher

[57] ABSTRACT

Indirect blood pressure measurement for a systolic or diastolic blood pressure is accomplished by making use of a true Korotkov sound determination. When three or four Korotkov sound signals are found in four successive heart pulses of a body, each of the three or four Korotkov sound signals is determined as a true Korotkov sound signal. A cuff pressure existing when the first true Korotkov sound appears is determined as a systolic blood pressure. Another cuff pressure existing when the last true Korotkov sound signal appears is determined as a diastolic blood pressure. The last true Korotkov sound signal is determined by counting three heart pulses unaccompanied by no Korotkov sound signals following the detection of the last true Korotkov sound appearance.

14 Claims, 3 Drawing Figures

METHOD AND APPARATUS FOR BLOOD PRESSURE MEASUREMENT INCLUDING A TRUE KOROTKOV SOUND DETECTOR

BACKGROUND OF THE INVENTION

The present invention relates to a method and apparatus for use in the clinical monitoring of an indirect blood pressure measurement of a body.

In a well known indirect blood pressure measurement system utilizing an inflatable cuff, the cuff pressure is increased until the artery is completely occluded, and while the cuff pressure is gradually decreased, a blood flow is started overcoming a certain cuff pressure and a Korotkov sound synchronized with a heart pulse appears. The cuff pressure value existing when the first Korotkov sound appears is defined as a systolic blood pressure. When the cuff pressure is further decreased to another certain cuff pressure, the Korotkov sound disappears and this latter cuff pressure value is defined as a diastolic blood pressure.

Most of the presently utilized automatic blood pressure measuring systems detect the appearance and disappearance of Korotkov sounds in order to determine the systolic and diastolic blood pressure levels as described above.

Since, the volume and quality of Korotkov sounds depends in large measure on the characteristic of each body, it is very difficult to precisely detect the appearance or disappearance of the Korotkov sounds from different individuals as signals separate from noise which may, for example, be caused by, a person touching the cuff.

Several prior art techniques have been developed which attempt to overcome this difficulty and precisely detect the appearance or disappearance of Korotkov sounds. In one technique, for example, when a Korotkov sound is found which is synchronized with a heart pulse, it is regarded as a true Korotkov sound and every other sound is deemed to be noise. A technique for determining a diastolic blood pressure is to note the cuff pressure existing when the last Korotkov sound appears if, after the above systolic blood pressure determination, no following Korotkov sounds appear after disappearance of a Korotkov sound for a few seconds, or if only heartbeat pulses appear.

None of the above techniques is adequate to determine a blood pressure, especially a diastolic blood pressure, where the time of disappearance of the Korotkov sound is not very clear. For example, in the technique where a disappearance is determined when no Korotkov sound is detected for a predetermined period of time, noise which appears within the predetermined period of time is often regarded as a Korotkov sound which begins a new predetermined period of time from the appearance of the noise which must transpire before the diastolic measurement is made. In other words, the noise appearing around the time of disappearance of a Korotkov sound causes the determination of a diasatolic blood pressure to be erroneous, even if the noise is relatively minor. Similar problems exist where the disappearance of Korotkov sound is determined when a predetermined number of heart pulses occur unaccompanied by Korotkov sounds.

The present invention, therefore, provides a determination system for a true Korotkov sound wherein a logic "1" is established when a Korotkov sound synchronized with a heart pulse is detected, and a logic "0" is established when only a heart pulse is detected unaccompanied by a Korotkov sound. The logic signals are successively stored in a four bit memory, and every Korotkov sound is determined as a true Korotkov sound when three or four "1" signals exist in the four consecutive bit locations in the memory. A systolic blood pressure determination is made following the true Korotkov sound determination from the cuff pressure existing when the first Korotkov sound among the three or four detected Korotkov sounds is detected. The present invention further provides a counter in addition to the above memory which counts a "0" signal applied to the memory and is reset by the true Korotkov sound determination. A determination for a diastolic blood pressure is effected when the counter counts up three "0" signals, following which the cuff pressure when the last "1" signal appears as a true Korotkov sound is regarded as a diastolic blood pressure. In other words, when a "1" signal synchronized with a heart pulse appears in the memory, it is not always regarded as a true Korotkov sound for the determination of a blood pressure. However, when two or more "1" signals are stored in the above memory prior to the above "1" signal, each "1" signal in the memory is regarded as a true Korotkov sound. Since each "1" signal except those meeting the above criteria is regarded as noise, the measurement of blood pressure is not disturbed. This is especially useful in the diastolic blood pressure determination.

It is therefore a general object of the present invention to provide a method and apparatus for accurately measuring a systolic and diastolic blood pressure.

It is specific object of the present invention to provide a method and apparatus for determining a true Korotkov sound for use in measuring blood pressure.

It is another object of the present invention to provide a method and apparatus for determining a diastolic blood pressure by counting a predetermined number of heart pulses unaccompanied by a Korotkov sound after a systolic blood pressure determination and the disappearance of true Korotkov sounds as the cuff pressure is decreased during measurement.

It is a further object of the present invention to provide a method and apparatus for measuring a blood pressure of the body when an auscultatory gap exists.

Further and more specific objects and advantages of the present invention will be apparent from the following more particular description of a preferred embodiment of the invention, which is illustrated in the accompanying drawings.

DESCRIPTION OF THE PREFERRED EMBODIMENT

Figures 1, 3:
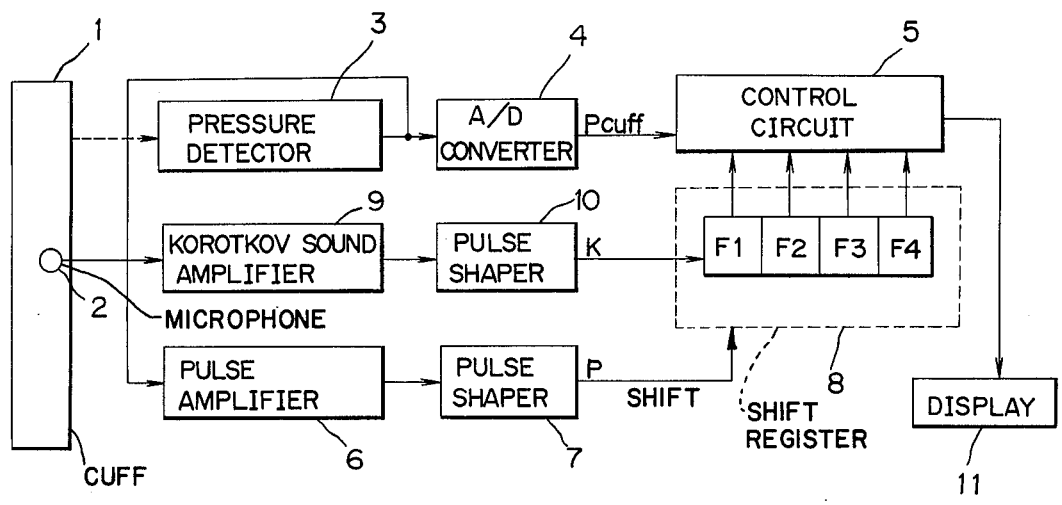
FIG. 1 is a schematic diagram showing an apparatus for indirect blood pressure measurement employing one embodiment of a Korotkov sound detecting system.
FIG. 3 is a table of a predetermined signal pattern in accordance with the present invention.

FIG. 1 shows a cuff 1 for occluding a blood flow which may be attached on the upper arm of the body. The cuff includes a microphone 2 positioned at the peripheral side of the occluded portion of the upper arm for detecting a Korotkov sound. A cuff pressure is applied to a pressure detector 3 via air which generates an analogue signal in response to the pressure in cuff 1. The analogue signal is converted to a digital signal through an A/D converter 4 and is applied to a control circuit 5 as described hereinafter. An output from the pressure detector 3 is introduced into a pulse amplifier 6. The amplifier 6 filters a heart pulse from the changing output signal wave of the pressure detector 3 and amplifies the heart pulse which is then applied to a pulse shaper 7. The pulse shaper 7 generates a heart pulse signal P which is waveform shaped and which becomes a shift signal for a shift register 8 described hereinafter.

An output from microphone 2 is applied to a Korotkov sound amplifier 9, which filters and amplifies a Korotkov sound signal. The Korotkov sound signal from the amplifier 9 has its waveform shaped by pulse shaper 10. The microphone 2, amplifier 9, and pulse shaper 10 compose a Korotkov sound detector, wherein an output (a Korotkov sound signal K) from the pulse shaper 10 is a logic "1" when a Korotkov sound (might be noise) is detected and a logic "0" when the Korotkov sound is not detected. The signal "1" or "0" from the Korotkov sound detector is applied to the input of shift register 8.

The shift register 8 is a four bit serial shift register having four registers F1, F2, F3, and F4. The first register F1 is set by a "1" signal when a Korotkov sound signal of "1" appears in synchronism with a heart pulse signal P or by "0" signal when only a heart pulse signal P appears. Data in the first register F1 is shifted to F2, F2 to F3, and F3 to F4 respectively. Accordingly the shift register 8 on measurement is set with a pattern of four bits of "1"'s and/or "0"'s depending on whether or not a Korotkov sound appeared in synchronism the last four heart pulse signals P. A parallel output from the shift register 8, namely the above four bit pattern (F1, F2, F3, F4), is applied to the control circuit 5. Control circuit 5 determines a systolic or diastolic blood pressure on the basis of the four bit pattern and the above cuff pressure as described hereinafter, and a value of the cuff pressure is fed to a display 11.

The above control circuit 5 in this embodiment is mainly composed of what is called a microprocessor which processes the signals inputted thereto for determining the systolic and diastolic blood pressures based on the output pattern from the above shift register 8.

Figure 2:
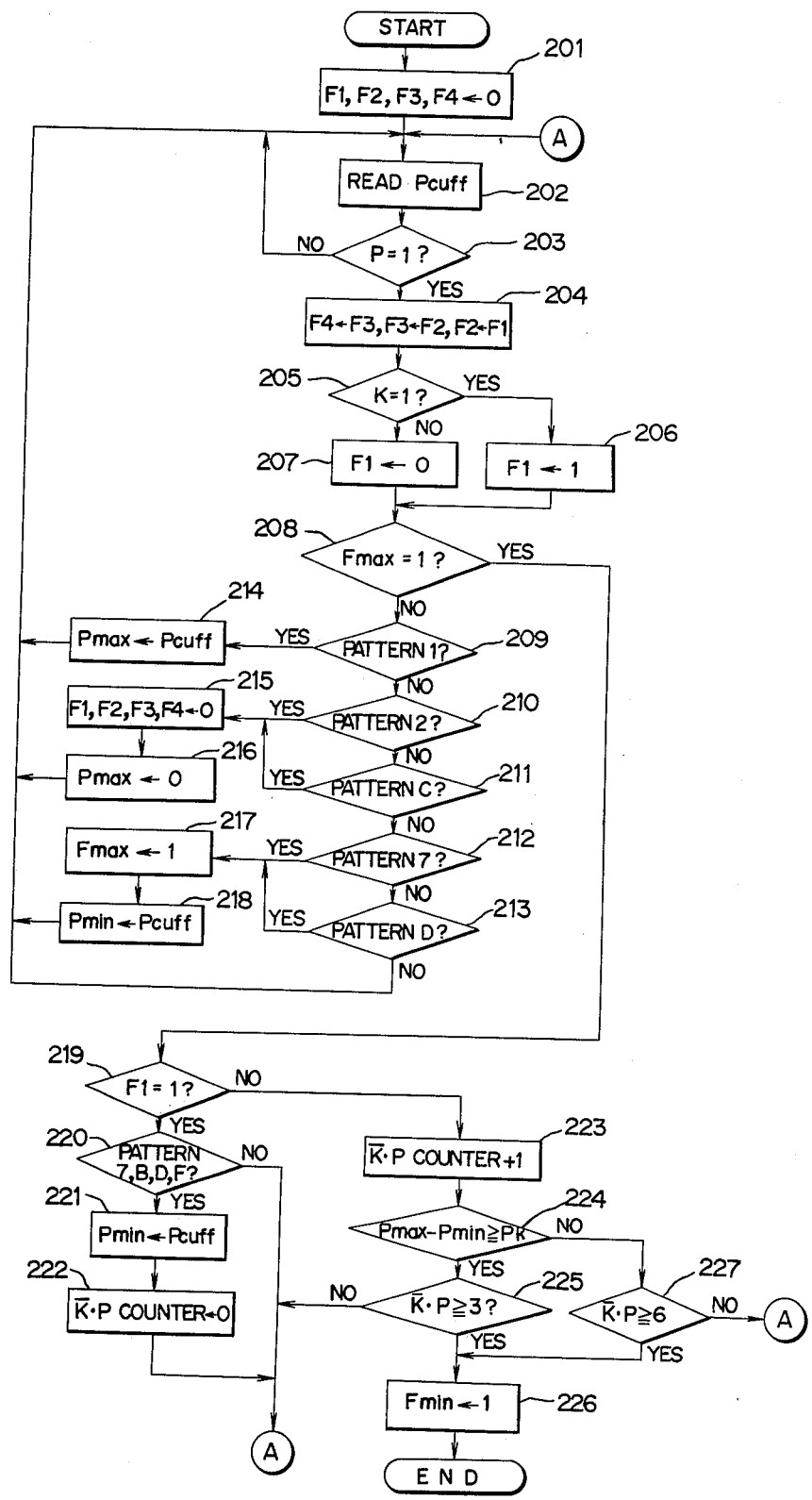
FIG. 2 is a flow diagram giving the steps in the determination of the systolic and diastolic blood pressure of a body.

Referring operation for FIG. 2 showing a flow chart for a control to determining a systolic and diastolic blood pressure, the present invention will be described in detail. FIG. 3 shows 16 possible patterns of the four bit output (F1, F2, F3, F4) of the shift register 8. Each pattern is identified by pattern numbers 0 to 9 and A to F which will be used in the following description.

The control operation for determination of a systolic blood pressure by the control circuit 5 will be described as follows. On start of a measurement the shift register 8 in FIG. 1 is reset and all four bit outputs are set to "0" in a first step 201. The step 201 also resets memories Pmax, Pmin and flags Fmax, Fmin which will be described in detail hereinafter (not shown in the step 201). In a second step 202 a cuff pressure Pcuff generated by the A/D converter 4 is read and temporally stored. In an inquiry step 203, an output signal of the pulse shaper 7 is examined, and if a heart pulse signal exists, P will equal "1"; that is, the point of appearance of a heart pulse is determined. A NO response to the inquiry 203 returns the control operation to the step 202 as the control circuit 5 waits for the heart pulse signal P.

When the inquiry step 203 detects an appearance of the heart pulse signal P, the step 204 shifts the data in the register F1 of the shift register 8 to F2, the data in the register F2 to F3, and the data in the register F3 to F4, respectively. Prior to this step each data in F1 to F4 was "0" (due to step 201) and after this step and the data in F2, F3, F4 remain unchanged. An inquiry step 205 receives the output status of the pulse shaper 10 and determines if a Korotkov sound signal K is "1," in other words, a Korotkov sound is detected. Since inquiry step 203 and inquiry step 205 occur at almost the same time, when heart pulse signal P and Korotkov sound signal K synchronously appear, a YES response is made in the inquiry 205 and "1" is set in the register F1 of the shift register 8 in a step 206. When only a heart pulse signal P appears, a NO response is made in the inquiry 205 and "0" is set operation in register F1 in a step 207. The control in the inquiry step 203 to step 207 performs the inputting and shifting operation for the shift register 8.

The step 206 or 207 flows to an inquiry step 208. The inquiry step 208 determines if a systolic blood pressure determination flag Fmax which is reset on start of the measurement is "1". At this time the flag Fmax should remain "0" because of the above described resetting and the next step is inquiry 209.

The inquiry step 209 determines if an output pattern (F1, F2, F3 and F4) from the shift register 8 is identical with the pattern 1 as shown in FIG. 3. A NO response to inquiry step 209 advances the process to an inquiry step 210 to determine if the contents of register 8 is identical with pattern 2. A NO response to the inquiry step 210 advances the process to an inquiry step 211 to determine if the register content is identical with pattern C. A NO response to the inquiry step 211 advances the process to an inquiry step 212 to determine if the register content is identical with pattern 7. A NO response to the inquiry step 212 advances the process to an inquiry 213 to determine if the register content is identical with pattern D. A NO response to the inquiry step 213 return the process to the step 202.

When the output pattern (F1, F2, F3 and F4) from the shift register 8 is determined to be identical with the pattern 1 in the inquiry step 209, namely, a Korotkov sound K synchronized with a heart pulse is detected at the first stage of the register (F1), it is assumed that there is a possibility that the Korotkov sound K is a true Korotkov sound for determining a blood pressure, and step 214 enables a systolic blood pressure memory Pmax to store the cuff pressure Pcuff read in the step 202 and returns the sequence to the step 202.

When the output pattern (F1, F2, F3 and F4) from the shift register 8 is determined to be identical with the pattern 2 in the inquiry step 210, namely, when no further Korotkov sound signal K, but a heart pulse signal P, is detected (F1=0) after the Korotkov sound signal K synchronized with the heart pulse signal P (F2=1), the process decides that the "1" signal in the register F2 was not true Korotkov sound for the blood pressure determination. In this case, a step 215 resets all stages of the shift register 8 to "0" and the step 216 clears the systolic blood pressure memory Pmax which had stored therein via step 214 the cuff pressure read in step 202. The processing sequence then returns to the step 202.

When the output pattern (F1, F2, F3 and F4) from the shift register 8 is determined to be identical with pattern C in the inquiry step 211, namely, when two Korotkov sound signals K synchronized with heart pulse signals P have been sequentially detected followed by the sequential detection of two heart pulse signals P unaccompanied by a Korotkov sound signal K, the process determines that each "1" signal in the register stage F3 and F4 was not a true Korotkov sound. When this occurs, the sequence returns to the step 202 through the step 215 and the step 216.

When the output pattern (F1, F2, F3 and F4) from the shift register 8 is determined to be identical with the pattern 7 in the inquiry step 212, namely, when three Korotkov sound signals K synchronized with a heart pulse signal P have been sequentially detected, or when the output pattern is determined to be identical with the pattern D, namely, when only a heart pulse signal P has been detected following the detection of two Korotkov sounds synchronized with heart pulse signals P and, thereafter, one Korotkov sound signal K synchronized with a heart pulse signal has been detected, the process determines that every "1" signal in the shift register 8 was a true Korotkov sound and in step 217 the systolic blood pressure determination flag Fmax is set to "1." The cuff pressure previously stored in the systolic blood pressure memory Pmax by the step 214 when the "1" signal in the register F3 in the pattern 7 appears or when the "1" signal in the register F4 in the pattern D appears, is displayed as a systolic blood pressure.

A step 218 subsequent to the step 217 allows a diastolic blood pressure memory Pmin to memorize the cuff pressure Pcuff read in the step 202, and returns the processing sequence to the step 202. The processing sequence advances to the inquiry step 208, through steps 202 to step 207. Step 208 now provides a YES response because the systolic blood pressure determination flag Fmax is set, and the sequence advances to a routine beginning with inquiry step 219 for a diastolic blood pressure determination.

The processing steps for determining a diastolic blood pressure in accordance with the present invention will now be described hereinafter.

The first step in the routine for determining a diastolic blood pressure is inquiry step 219, which determines if the first stage F1 of the shift register 8 is set to "1." In other words, the process sequence determines if the last input signal is a Korotkov sound signal K synchronized with a heart pulse signal P, or if it is only a heart pulse signal. If it is just after the systolic blood pressure determination, a YES response to the inquiry 219 is made and the sequence proceeds to an inquiry step 220.

The inquiry step 220 determines if the output pattern (F1, F2, F3 and F4) is identical to any one of the patterns 7, B, D, or F. In other words, the process determines if a "1" signal is set in the register F1 and there are two or more "1" signals in the other three bit stages F2, F3 and F4. When Korotkov sounds are normally generated, the output pattern (F1, F2, F3 and F4) corresponds to one of the patterns 7, B, D, or F. As a result, the inquiry step 220 provides a YES response, which indicates that three or more "1" signals, including the last "1" input in the four bit pattern, exist and each "1" signal should be a true Korotkov sound signal. A step 221 responsive to the YES response from inquiry step 220 stores a cuff, pressure Pcuff which was read in the step 202 when the "1" signal as the last Korotkov sound appears in the stage F1, into the diastolic blood pressure memory Pmin. In next step 222 a counter marked as a $\overline{K}\cdot P$ counter in FIG. 2 is reset and the sequence is returned to the step 202.

A NO response to the inquiry 220 indicates that, regardless of the fact that the last input signal in the stage F1 is a "1" signal, it is treated as possibly not being a true Korotkov sound when two or more "0" signals exist in the other advanced three bit registers F2, F3 and F4. At that time a pressure data in the diastolic blood pressure memory Pmin is not revised, and the sequence is returned to the step 202 without resetting the $\overline{K}\cdot P$ counter.

A NO response to the inquiry step 219 indicating that only a heart pulse signal P has been detected, in position F1, i.e., the last input signal in the register F1 of the shift register 8 is "0", is introduced to a step 223. In the step 223 the $\overline{K}\cdot P$ counter adds one to its stored count. In other words, the $\overline{K}\cdot P$ counter counts the number of "0" signals applied to the shift register 8 when the Korotkov sound signal K is "0" and the heart pulse signal P is "1." As described above, the $\overline{K}\cdot P$ counter is reset when the "1" signal determined to be a true Korotkov sound enters the shift register 8.

In an inquiry step 224 subsequent to the step 223, a determination is made as to whether the difference value between the pressure value stored in the systolic blood pressure memory Pmax as a systolic blood pressure and the pressure value stored in the diastolic blood pressure memory Pmin is greater than or equal to a predetermined reference value. The significance of the inquiry 224 will be described hereinafter in detail. In the normal case, the inquiry step 224 provides a YES response.

The YES response to the Inquiry 224 is introduced to an inquiry step 225 which determines if a counted value in the $\overline{K}\cdot P$ counter is three or more. The inquiry step 225 ignores the fact that a "1" signal not determined as a true Korotkov sound may be applied to the shift register 8, and determines if the number of "0" signals applied to the shift register 8 reaches three or more after the last "1" signal determined as a true Korotkov sound is applied to the shift register 8. When the counted value in the $\overline{K}\cdot P$ counter is two or less, it is determined that a possibility exists that a further "1" signal determined as a true Korotkov signal might still be applied to the shift register 8. In this case a NO response to the inquiry 225 is made and the process sequence is returned to the step 202.

Once the counted value in the $\overline{K}\cdot P$ counter reaches three or more and the inquiry step 225 provides a YES response, any "1" signals existing during the $\overline{K}\cdot P$ counter's counting up to three which have not been determined to be true Korotkov sounds are ignored as noise and the process sequence determines that Korotkov sounds have completely disappeared. In the next step 226 the diastolic blood pressure determination flag Fmin (which was reset at the start of the measurement process) is set to "1." When this occurs, the pressure data stored in the diastolic blood pressure memory, namely, the cuff pressure stored when the last "1" signal determined as a true Korotkov sound appears, is displayed as a diastolic blood pressure reading.

A control operation for a diastolic blood pressure determination as described above will be described hereinafter in accordance with the situation where a series of input signals 1, 2, 3, ... is sequentially applied to the shift register 8. In the following description, the inquiry 224 is assumed to make a YES response.

| 1 | 1 | 1 | 1 | 1 | 1 | 0 | 1 | 1 | 0 | 1 | 0 | 1 | 0 | 1 | 0 | 0 | 0 |
|---|---|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 | 17 | 18 |

These inputs occur after a systolic blood pressure has been determined. The inputs from 1 to 6 continue as "1" indicating that a normal detection for Korotkov sounds is being made. In this state, whenever each of the "1" signals appears, the cuff pressure at the time is read into the diastolic blood pressure memory Pmin and the $\overline{K \cdot P}$ counter is reset. When a signal "0" at the seventh input appears, the $\overline{K \cdot P}$ counter counts one. When the eighth input signal of "1" appears, however, this "1" signal is determined as a true Korotkov sound because there are two "1" signals in the advanced three bits (5 to 7). As a result, the data in the diasstolic blood pressure memory Pmin is revised and $\overline{K \cdot P}$ is reset. When the 10th input signal of "0" appears, $\overline{K \cdot P}$ counter counts one; however, as described above when the 11th input signal of "1" determined as a true Korotkov sound appears, the $\overline{K \cdot P}$ counter is reset and the data in the diastolic blood pressure memory Pmin is revised.

When the 12th input signal of "0" appears, the $\overline{K \cdot P}$ counter is stepped and the counted value will become 1. The 13th input signal is "1," but there is only one "1" signal in the preceding three bits, so that the input signal is not determined as a true Korotkov sound; therefore, the $\overline{K \cdot P}$ counter is not reset and the diastolic blood pressure memory Pmin is not revised. Accordingly, the 14th input signal of "0" allows the $\overline{K \cdot P}$ counter to step again and the counted value will become 2. Its succeeding 15th input signal of "1" is not decided as a true Korotkov sound, because there is only one "1" in the preceding three bits as previously described.

Therefore, on the 16th input signal of "0," the $\overline{K \cdot P}$ counter steps and its counted value becomes 3, resulting in the diastolic blood pressure determination flag Fmin being set to a "1" and the signals of "1" on the inputs 13 and 15 are ignored as noise. Following this, the data in data in the diastolic blood pressure memory Pmin which is the cuff pressure stored when the 11th input signal of "1" (the last true Korotkov sound) appears is displayed as a diastolic blood pressure.

The significance in the control operation of inquiry step 224 will be described hereinafter. This inquiry is mainly designed so that the control operation may compensate for the occurrence of an auscultation gap. An auscultation gap is a phenomenon whereby a Korotkov sound is temporally not detected as decreasing cuff pressure is applied on the way from the systolic blood pressure level to the diastolic blood pressure level but a Korotkov sound again appears. This auscultation gap is often found in hypertensive patients. Accordingly when a "0" signal is applied to the shift register 8 in spite of a minor cuff pressure decrease after the systolic blood pressure determination, namely, when the last input signal is "0" and the inquiry 224 provides a NO response indicating that the difference between the already decided systolic blood pressure and a cuff pressure (almost the cuff pressure at that time) then stored in the diastolic blood pressure memory Pmin is less than a reference value Pk, the process determines that the "0" input signal has the possibility that it is based on the above auscultation gap. Although in the inquiry step 225 a complete disappearance of Korotkov sound is determined when the $\overline{K \cdot P}$ counter counts up 3, an inquiry step 227 determines if a counted value in the $\overline{K \cdot P}$ counter is 6 or more and, returns the sequence to the step 202 when it is less than 6, and advances the sequence to the step 226 to set the diastolic blood pressure determination flag Fmin when it is 6 or more. In this manner, an auscultation gap is found and a wrong measurement based on it is avoided. The above reference value Pk depends upon patients, but 15 to 25 mm Hg, especially 20 mm Hg, is confirmed as a good value in practice.

As above-mentioned, the systolic or diastolic blood pressure determination in the present invention is based on the true Korotkov sound which is determined by the three or four "1" signals existing in the above four bit register and, not by simply detecting the synchronism of a Korotkov sound, detected from the Korotkov sound detector, with a heart pulse. Through the present embodiment does not include the pattern B in the patterns from the inquiry step 209 to the inquiry step 213, the present invention may include it in the systolic blood pressure determination since there three "1" signals would exist in the shift register 8. When in the diastolic blood pressure determination a "1" input signal, not yet decided as a true Korotkov sound, appears, the "1" input signal has a possibility which might be later determined as a true Korotkov sound and, therefore, it is neglected in a determination for the disappearance of a Korotkov sound. The number of times the "0" signal after the last "1" signal being determined as a true Korotkov sound is applied to register 8 is counted; the determination for the disappearance Korotkov sounds is made when the counted value of "0"'s is three, after which the cuff pressure occurring at the appearance of the last "1" signal, determined as a true Korotkov sound is regarded as the diastolic blood pressure. As a result, a precise diastolic blood pressure measurement is performed unimpeded by the influence of noise appearing at times near the time at which the diastolic blood pressure level occurs. The present embodiment is described utilizing a microprocessor processing a main control in software, but the present invention may be practiced with a hardware logic circuit device performing like functions.

Although the present invention has been described in its preferred embodiment, it should be understood by those skilled in the art that the present invention is not limited to the present embodiment and various changes and modifications may be made in the present invention without departing the spirit and scope thereof.

What is claimed is:

1. A method for determining the presence of true Korotkov sounds for use in a blood pressure measurement system comprising the steps of:
   detecting sequentially occurring heart pulse signals and Korotkov sounds emitted from a body,
   determining when any detected heart pulse signal occurs in time synchronism with a detected Korotkov sound,
   examining four successively detected heart pulse signals and any associated time synchronized detected Korotkov sounds to determine whether three or four Korotkov sounds were time synchronized with said four detected heart pulse signals, and determining that each of the Korotkov sound signals associated with said four detected heart pulse signals is a true Korotkov sound signal when three or four time synchronized Korotkov sound signals are found in said examination.

2. A method as set forth in claim 1 further comprising the steps of storing a cuff pressure value when the first true Korotkov signal of said three or four Korotkov sound signals determined as true Korotkov sound signals appears, and providing that said stored cuff pressure value as a measurement of systolic blood pressure.

3. A method as set forth in claim 2 wherein said true Korotkov sound determination is made when the first and second time synchronized Korotkov sound signals of said three or four time synchronized Korotkov sound signals appear consecutively.

4. A method as set forth in claim 2 further comprising the steps of holding a cuff pressure value whenever said true Korotkov sound signal determination is made after said systolic blood pressure measurement, counting successively occurring heart pulse signals unaccompanied by an associated time synchronized Korotkov sound signal up to a predetermined number, said counting being reset whenever said true Korotkov sound signal determination is made, and determining that a last held cuff pressure value is a measured diastolic blood pressure when said predetermined number of heart pulse signals is counted.

5. A method as set forth in claim 4 wherein said predetermined number is three.

6. A method as set forth in claim 4 further comprising the step of determining the difference between a measured systolic blood pressure and a last held cuff pressure and using six as said predetermined number when said difference is less than a predetermined value.

7. A method as set forth in claim 6 wherein said predetermined value is 20 mm Hg.

8. An apparatus for determining the presence of true Korotkov sounds for use in a blood pressure measurement system comprising:

an inflatable blood pressure cuff, means associated with said cuff for detecting the successive emission of Korotkov sounds from a body and for providing a "1" signal when a Korotkov sound signal is detected and a "0" when no Korotkov sound signal is detected, means associated with said cuff for detecting the successive emission of heart pulse signals from a body and for providing a pulse signal when said heart pulse signals occur, a four stage shift register means for serially receiving at an input thereof the output from said means for detecting Korotkov sound signals, said register means being responsive to said pulse signal to shift the contents thereof, and means for examining said four steps of said shift register and for determining that each "1" signal in said examined four stages represents the occurrence of a true Korotkov sound when either three or four "1" signals are contained in said four stages.

9. An apparatus as set forth in claim 8 further comprising means for determining the pressure within said cuff as a systolic blood pressure when the first said true Korotkov sound is received in said four stages of said shift register means.

10. An apparatus as set forth in claim 9 wherein said means for determining determines that each "1" stores in said four stages is a true Korotkov sound signal when the first and second "1" signals of said three or four "1" signals appear consecutively in said four stages.

11. An apparatus as set forth in claim 8 further comprising diastolic blood pressure storage means for holding a cuff pressure value whenever a "1" signal determined as a true Korotkov sound by said examining and determining means is applied to said shift register means, counting means for counting every "0" signal applied to said shift register means and for generating an output signal upon counting up to a predetermined number, said counting means being reset when a "1" signal determined as a true Korotkov sound by said examining and determining means is applied to said shift register means, and means for providing the cuff pressure value last held in said storage means as a diastolic blood pressure when said output signal from said counting means is generated.

12. An apparatus as set forth in claim 11 wherein said predetermined number is three.

13. An apparatus as set forth in claim 11 further comprising systolic blood pressure storage means for storing a cuff pressure value when the first "1" signal of said three or four "1" signals determined to represent true Korotkov sounds appears and for providing said stored cuff pressure value as a measurement of systolic blood pressure, means for determining the difference between a measured systolic blood pressure and a cuff pressure held in said diastolic blood pressure storage means, and means for ensuring that said predetermined number is six when said difference is less than a predetermined value.

14. An apparatus as set forth in claim 13 wherein said predetermined value is 20 mm Hg.

* * * * *